United States Patent [19]

Groen

[11] Patent Number: 5,717,081
[45] Date of Patent: Feb. 10, 1998

[54] PROCESS FOR PRODUCING AN ALKYLGLYCOSIDE USING A PERVAPORATION MEMBRANE TO REMOVE REACTION WATER

[75] Inventor: Johannes Groen, Huizen, Netherlands

[73] Assignee: Unichema Chemie B.V., Gouda, Netherlands

[21] Appl. No.: 596,209

[22] PCT Filed: Sep. 8, 1994

[86] PCT No.: PCT/EP94/03028

§ 371 Date: Feb. 14, 1996

§ 102(e) Date: Feb. 14, 1996

[87] PCT Pub. No.: WO95/07915

PCT Pub. Date: Mar. 23, 1995

[30] Foreign Application Priority Data

Sep. 17, 1993 [EP] European Pat. Off. ............ 93202696

[51] Int. Cl.⁶ .......................... C07H 15/04; C07H 1/06
[52] U.S. Cl. .................. 536/18.5; 510/470; 536/18.6; 536/120; 536/124
[58] Field of Search ..................... 536/18.5, 18.6, 536/124, 120; 252/174.17; 510/470

[56] References Cited

U.S. PATENT DOCUMENTS

| 4,721,780 | 1/1988 | McDaniel et al. | 536/18.6 |
| 4,987,225 | 1/1991 | Pickens et al. | 536/124 |
| 5,459,249 | 10/1995 | Bergfeld et al. | 536/18.6 |
| 5,496,932 | 3/1996 | McCurry et al. | 536/18.5 |
| 5,512,666 | 4/1996 | McCurry et al. | 536/18.6 |
| 5,519,124 | 5/1996 | McCurry et al. | 536/18.5 |

FOREIGN PATENT DOCUMENTS

| 498 509 | 8/1992 | European Pat. Off. |
| 91 02046 | 2/1991 | WIPO |
| 93 12865 | 7/1993 | WIPO |
| 9523871 | 9/1995 | WIPO |

OTHER PUBLICATIONS

Nakagawa, et al: "Method for preparation of ether compounds and purification by pervaporation", Chemical Abstracts, vol. 118, No. 17, Apr. 26, 1993, abstract No. 168695j, p. 839, col. 2, see abstract & JP.A.04 253 931.

*Primary Examiner*—John Kight
*Assistant Examiner*—Howard C. Lee
*Attorney, Agent, or Firm*—Cushman Darby & Cushman IP Group Pillsbury Madison & Sutro LLP

[57] ABSTRACT

In a process for producing an alkylglycoside by glycosidation of a saccharide or reglycosidation of a lower alkylglycoside in the presence of an acidic catalyst, the water of the reactor is removed by pervaporation. Also an apparatus for carrying out the reaction has been described.

13 Claims, 1 Drawing Sheet

PROCESS FOR PRODUCING AN ALKYLGLYCOSIDE USING A PERVAPORATION MEMBRANE TO REMOVE REACTION WATER

This application claims benefit of international application PCT/EP94/03028, filed Sep. 8, 1994.

The present invention relates to a process for producing an alkylglycoside by reaction of an alcohol with a saccharide or reaction of a higher alcohol with a lower alkylglycoside in the presence of an acidic catalyst and to the alkylglycosides thus produced, as well as to their use in surface-active compositions. The invention also relates to an apparatus for carrying out the process of the present invention.

It is known to prepare alkylglycosides from a saccharide and alcohols by glycosidation or by reglycosidation of lower alkylglycosides and higher alcohols in the presence of acidic catalysts. A review of the synthesis of a number of alkylglycosides was published by Dr Th. Böcker and Prof Dr T. Thiem in Tenside Surf. Det., Vol. 26, No. 5, 318–324 (1989).

One of the problems in the production of alkylglycosides is the quick removal of the water formed in the reaction, so that the reaction rate will be economically acceptable.

It has now been found alkylglycosides can be obtained at a higher reaction rate and a higher final conversion, by using pervaporation to continuously remove the reaction water. In pervaporation, a liquid feed (containing a more permeable and a less permeable component) is maintained in contact with a permeable membrane and a pressure drop is maintained across the membrane. Out of the feed liquid the component to be removed passes through the membrane. The permeate which passes through the membrane and is in vapor form, may be recovered by condensation at low temperature or may be carried away by using a moving stream of gas.

Preferably, the permeate side of the membrane is maintained at a low pressure in the magnitude of 5 mm Hg (0.67 KPa). The residual feed kept in the separation unit is called the retentate or concentrate. In the process of vapor permeation, the feed mixture is first evaporated and then the vapor is passed along the membrane.

The pervaporation process has been described in more detail in W. S. Winston Ho and K. k. Sirkar "Membrane Handbook", Van Nostrund Reinhold Publishing Corp., New York, 1992 on pages 105–159.

Therefore, the present invention relates to a process for producing an alkylglycoside by reaction of an alcohol with a saccharide or reaction of a higher alcohol with a lower alkylglycoside in the presence of an acidic catalyst, which is characterized in that at least one pervaporation membrane is provided in the process apparatus, such that the water of reaction is continuously removed from the reaction mixture through the membrane.

The saccharide which can be used in the process of the present invention comprises preferably water-soluble monosaccharides, such as glucose, fructose, galactose, mannose, xylose, arabinose and the like, as well as preferably water-soluble polysaccharides such as sucrose, maltose, maltotriose, lactose, and the like and also mixtures of monosaccharides and polysaccharides. The saccharide material is preferably used in the form of a slurry or dispersion in alcohol from which the alkylglycoside is formed. The use of glucose and fructose is preferred.

As the alcohol a monohydric, saturated, straight or branched chain alcohol having from 1 to 6 carbon atoms is used, such as methanol, ethanol, propanol, iso-propanol, butanol, and mixtures thereof. Also polyhydric saturated aliphatic alcohols like ethylene glycols, propylene glycols, glycerol, and the like may be used, in which case hydroxyalkylglycosides are formed.

As the lower alkylglycoside there may be used a $C_1$–$C_6$ alkylglycoside, like methylglycoside, ethylglycoside, hexylglycoside, and the like.

The higher alcohol which is used in the reglycosidation reaction according to the present invention is selected from the straight or branched chain monohydric alcohols, having from 8 to 24 carbon atoms, like octanol, dodecyl alcohol, and the like. Usually, mixtures of fatty alcohols having from 12 to 18 carbon atoms are used.

In general, a reaction temperature between 60° C. and 180° C. is used, and preferably the reaction is effected at 80° C. to 140° C. The reaction can be carried out at superatmospheric, atmospheric and subatmospheric pressure. Also an inert gas atmosphere may be applied. As the acidic catalyst a liquid or solid, inorganic or organic acid can be used, such as sulphuric acid, phosphoric acid, sulphonic acids, ion exchange resins (e.g. those of the styrene divinyl benzene type), acid activated bleaching earth, acid zeolites (such as high pore volume silica-alumina cracking catalysts) and mixtures thereof. The catalyst can also be provided in the form of a so-called fixed bed in the reactor. The use of ion exchange resins as catalyst has the advantage that the membrane is not subject to attack by acid, thus giving more flexibility in the selection of suitable membranes.

The reaction may be performed in a stirred tank reactor or a series of stirred tank reactors, but also in a gelling film evaporator. The reactor is followed by a pervaporation unit, out of which the retentate can be recirculated into the reactor. The permeate can be subjected to further treatments. If required, a filtration unit may be provided between the reactor and the pervaporation unit.

The pervaporation takes place across a pervaporation membrane. This membrane may be of any of the commercially available varieties, provided that they have adequate resistance to the reaction mixture. The pervaporation membrane is typicaly a multilayer membrane, comprising an active outer layer of (modified) polyvinyl alcohol, a porous backing layer which may be a polyacrylonitrile layer and a support layer which may be a non-woven polyester, like poly (ethylene terephthalate). Also other suitable types of membranes may be used. Alternatively, the active pervaporation membrane can be attached to the inside surface of a ceramic microfiltration module. In order to achieve optimum results from the process according to the present invention, the pressure at the low pressure side of the membrane may suitably be from 1 to 100 mbar, preferably from 1 to 20 mbar. The pervaporation is preferably started if a clear reaction mixture is obtained.

A suitable apparatus for carrying out the process of the present invention comprises a glycosidation or reglycosidation reactor, means for feeding the saccharide or lower alkylglycoside and the alcohol or the higher alcohol and, optionally, an inert gas to the reactor, and a pervaporation device connected to the reactor to receive the glycosidation or reglycosidation reaction product mixture therefrom and comprising a pervaporation membrane and means for removing the reaction water from the pervaporation device and means for recirculating the reaction mixture retentate from the pervaporation device into the reactor.

It is preferred that during the action of the pervaporation device no solid saccharide or catalyst is present in the glycosidation or reglycosidation reaction mixture and to this purpose it is beneficial to include a filtration device between the reactor and the pervaporation device.

The invention will now be illustrated on hand of the following examples.

EXAMPLE I 0.945 kg of glucose were mixed with 0.5% by weight (based on the weight of the glucose) of P-toluene sulphonic acid and this mixture was brought into a stainless steel jacketed vessel with a volume of 5 liters filled with 1200 grams of absolute ethanol. The vessel was equipped with a variable speed stirrer and the necessary inlet and outlet tubes. The glucose in ethanol slurry was mixed with 1415 grams of absolute ethanol and the mixture was heated to 100° C. while stirring until all glucose had been dissolved in the reaction mixture. Two hours after the reaction mixture had reached a temperature of 100° C., it was pumped continuously for 22 hours over the surface of a pervaporation membrane (Celfa CMC-A membrane, active area 0.04 m$^2$, Trade Mark, ex CM-CELFA Membrantrenntechnik AG.Switzerland) and recycled to the reaction vessel. The pressure at the feed side of the pervaporation membrane was 2 bars. At the other side of the membrane a pressure of 1 mbar was maintained using a vacuum pump. The water removed by the membrane was condensed and collected in a glass flask.

Figure 1:
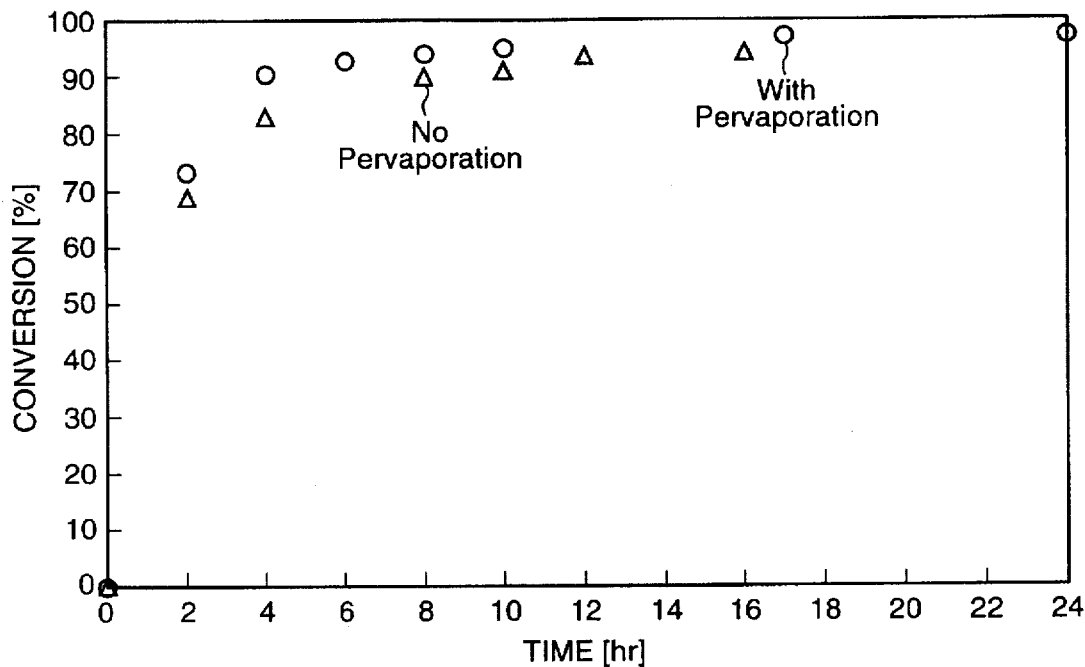
FIGS. 1 and 2 are graphs illustrating the effects on percent conversion (FIG. 1) and water content (FIG. 2) when pervaporation is used (O) or not used (Δ) in the process.

In a second experiment, the reaction was carried out under the same conditions, but not using the pervaporation device. In FIG. 1, the conversion as a function of time is shown for both experiments. It can be seen that with the application of pervaporation a higher final conversion was obtained and also a shorter process time was needed to reach a certain conversion.

Figure 2:
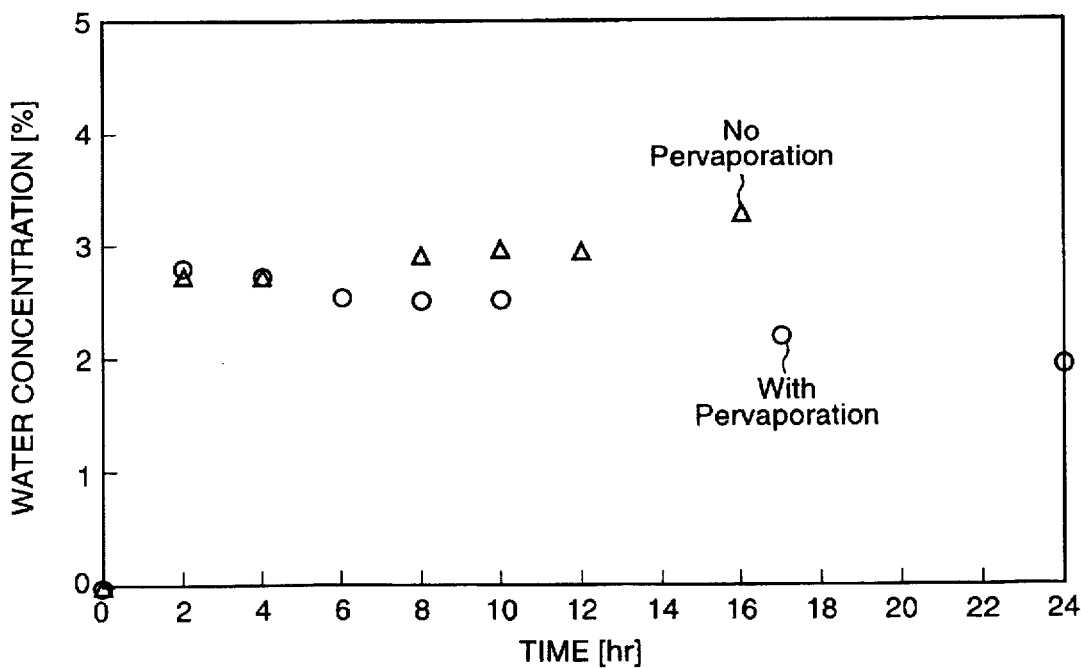

In FIG. 2 the water content in the reaction mixture has been shown. Without pervaporation, the water content increased progressively during the reaction. With the pervaporation device coupled to the reactor the water concentration first increased, then reached a maximum and subsequently decreased progressively during the reaction. The lower water content in the reaction mixture decreased the rate of the reverse chemical reaction and hence gave a higher overall reaction rate for the formation of ethyl glucoside.

EXAMPLE II

Example I was repeated, but this time a different pervaporation membrane (Carbone-Lorraine Type CL 1000, Trade Mark, ex Le Carbone-Lorraine S.A., Paris, France) was used. After 24 hours a conversion of 98.9% of ethylglucoside was obtained; the water content in the reactor was 0.20% by weight and the water concentration in the permeate was 52.4% by weight (water flux 0.03 kg/m$^2$h).

If more membrane area is installed for a given reactor size, the water will be removed from the reactor at a higher rate, resulting in higher reaction rates and a higher equilibrium conversion. At the same time, however, the pervaporation unit will be more expensive. There is therefore an economic optimum membrane size for a given reactor size. With reduced reactor loading, hence increased ratio between the membrane area and the reactor size, a higher reaction rate and higher final conversion are reached.

I claim:

1. A process for producing an alkylglycoside by reaction of an alcohol with a saccharide (glycosidation) or reaction of a higher alcohol with a lower alkylglycoside (reglycosidation) in the presence of an acidic catalyst, characterized in that at least one pervaporation membrane is provided in the process apparatus, such that the water of the reaction is continuously removed from the reaction mixture through the membrane.

2. A process according to claim 1, in which the saccharide is a monosaccharide or a polysaccharide.

3. A process according to claim 1, in which the polysaccharide is a water-soluble saccharide.

4. A process according to claim 1, in which the saccharide is glucose or fructose.

5. A process according to claim 1, in which the alcohol is selected from the group consisting of saturated, straight or branched chain monohydric alcohols having from 1 to 6 carbon atoms and saturated, aliphatic polyhydric alcohols.

6. A process according to claim 1, in which the higher alcohol is selected from straight or branched chain monohydric alcohols having from 8 to 24 carbon atoms.

7. A process according to claim 1, in which the lower alkylglycoside is a glycoside having a straight or branched chain $C_1-C_6$ alkylether group.

8. A process according to claim 1, in which the glycosidation or reglycosidation reaction is effected at a temperature from 60° C. to 180° C.

9. A process according to claim 1, in which the glycosidation or reglycosidation reaction is effected at a temperature from 80° C. to 140° C.

10. A process according to claim 1, in which the pervaporation membrane comprises a polyvinyl alcohol active layer, a polyacrylonitrile backing layer and a non-woven polyester support layer.

11. A process according to claim 1, in which the pervaporation membrane is attached to the inside surface of a ceramic microfiltration module.

12. A process according to claim 1, in which the pressure at the low pressure side of the pervaporation membrane is from 1 to 100 mbar.

13. A process according to claim 1, in which during the pervaporation action no solid saccharide or catalyst is present in the reaction mixture by passing the reaction mixture through a filtering device prior to processing through the pervaporation membrane.

* * * * *